Figure 1:
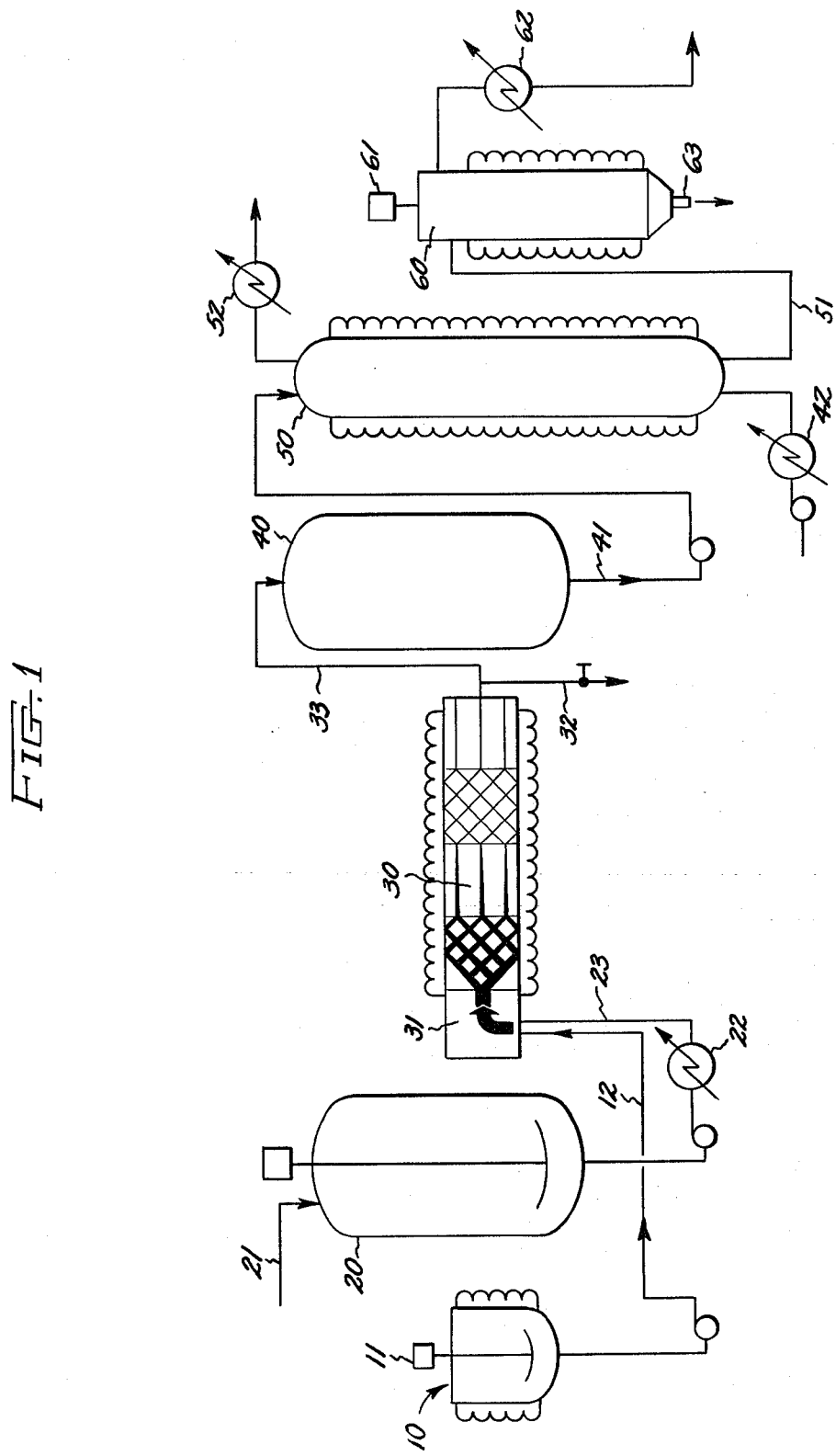

United States Patent [19]

Webb et al.

[11] 4,318,857

[45] Mar. 9, 1982

[54] METHOD FOR MAKING AROMATIC BIS (ETHER ANHYDRIDES)

[75] Inventors: Jimmy L. Webb, Ballston Lake, N.Y.; Donald L. Phipps, Pittsfield, Mass.

[73] Assignee: General Electric Company, Schenectady, N.Y.

[21] Appl. No.: 251,019

[22] Filed: Apr. 3, 1981

[51] Int. Cl.³ .......................................... C07D 307/83
[52] U.S. Cl. .................................................. 260/346.3
[58] Field of Search ....................................... 260/346.3

[56] References Cited

U.S. PATENT DOCUMENTS 4,116,980  9/1978  Webb ................................. 260/346.3
4,128,574  12/1978  Markezich et al. ................. 562/473

Primary Examiner—Henry R. Jiles
Assistant Examiner—Bernard Dentz
Attorney, Agent, or Firm—William A. Teoli; James C. Davis, Jr.

[57] ABSTRACT

A method is provided for controlling the build-up in concentration of triorganoamine exchange catalyst in an organic extraction solvent used in the extraction of aromatic bis(ether phthalimide) and N-organo substituted phthalimide from an imide-anhydride exchange reaction mixture. The concentration of the triorganoamine exchange catalyst is controlled in the extracting organic solvent by extracting the organic solvent with an aqueous mixture of phthalic acid and triorganoamine and thereafter recycling the organic solvent to the extractor.

6 Claims, 2 Drawing Figures

METHOD FOR MAKING AROMATIC BIS (ETHER ANHYDRIDES)

CROSS REFERENCE TO RELATED APPLICATIONS

Reference is made to copending applications Ser. No. 250,804, filed Apr. 3, 1981 and Ser. No. 253,446, filed Apr. 13, 1981 of Jimmy L. Webb and Bharat M. Mehta, for Method for Making Aromatic Bis(Ether Anhydride)s, and assigned to the same assignee as the present invention.

BACKGROUND OF THE INVENTION

In copending application RD-13036 there is taught a method of making aromatic bis(ether phthalic anhydride) by effecting reaction between molten aromatic bis(ether N-organophthalimide) and an aqueous phthalic acid solution containing an imide-anhydride exchange catalyst, for example, a triorganoamine. Upon reaching equilibrium, the exchange reaction mixture is extracted with an organic solvent to effect the removal of unreacted aromatic bis(ether N-organophthalimide) and N-organophthalimide.

Experience has shown that when the imideanhydride exchange mixture has been extracted several times to provide for aromatic bis(ether phthalic anhydride) having acceptable purity, the concentration of the triorganoamine exchange catalyst continues to build-up in the recycled organic solvent and cause a significant catalyst loss and eventually interferes with the recovery of the aromatic bis(ether phthalic anhydride).

The present invention is based on the discovery that the build-up in concentration of the triorganoamine catalyst in the organic solvent used to extract unreacted aromatic bis imide and N-organophthalimide reaction product can be controlled. The triorganoamine catalyst recovery from the organic solvent can be achieved if the extracting organic solvent is itself extracted with an aqueous phthalic acid solution before it is recycled. Experience has shown that treating the extracting organic solvent having 1-20% by weight of triorganoamine with 20-35% by weight of aqueous phthalic acid solution removes 85-95% triorganoamine from the organic solvent. The resulting extracted organic solvent after subsequent processing to effect imide removal, can then be recycled to the extraction column. The aqueous mixture of phthalic acid and triorganoamine catalyst containing additional triorganoamine extracted from the organic solvent can be recycled to the imide-anhydride exchange reactor.

STATEMENT OF THE INVENTION

In the process of making aromatic bis(ether phthalic anhydride) comprising
(1) effecting an exxchange reaction between aromatic bis(ether N-organophthalimide) and phthalic anhydride in the presence of water and triorganoamine exchange catalyst,
(2) extracting the resulting aqueous exchange reaction mixture with an organic solvent,
(3) separating the resulting aromatic bis(ether phthalic acid), phthalic acid and triorganoamine catalyst in the aqueous phase from the resulting N-organo phthalimide, unreacted aromatic bis(ether N-organophthalimide) and triorganoamine in the organic phase,
(4) recovering the aromatic bis(ether phthalic acid) from the aqueous phase and the aromatic bis(ether phthalimide) and N-organo phthalimide from the organic phase, and
(5) recycling the phthalic acid and triorganoamine catalyst to the exchange mixture of step (1) and recycling the organic solvent to effect extraction of the aqueous exchange reaction mixture of step (2), whereby a constant concentration build-up occurs of the triorganoamine exchange catalyst in the extracting organic solvent, which results in a reduction in the rate of production of the aromatic bis(ether phthalic anhydride), the improvement which comprises, extracting the organic solvent before it is recycled to the extractor in step (2) with an aqueous mixture of phthalic acid and triorganoamine and thereafter recycling the organic solvent to the extractor of step (2), and the aqueous phthalic acid-triorganoamine catalyst to the exchange reaction of step (1) whereby a build-up of the concentration of the triorganoamine in the organic solvent is avoided and a recycling of the recovered triorganoamine exchange catalyst to the exchange reaction is effected.

There are included within the aromatic bis(ether anhydride)s which can be made in accordance with the practice of the present invention, compounds of the formula,

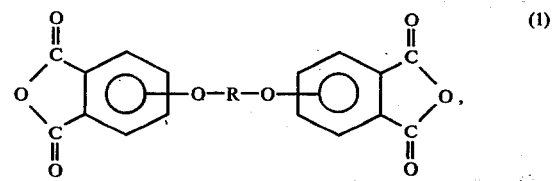

where R is a $C_{(6-30)}$ divalent aromatic organic radical.

Among the aromatic bis(ether phthalimide)s which can be used in the practice of the present invention to make the dianhydrides of formula (1) by effecting an exchange reaction with phthalic anhydride in the presence of water and a triorganoamine catalyst are compounds of the formula,

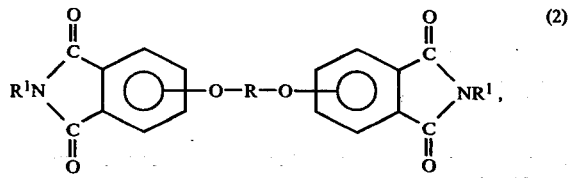

where R is as previously defined and $R^1$ is a monovalent organo radical selected from the class consisting of $C_{(1-8)}$ alkyl radicals, and $C_{(6-13)}$ aromatic radicals.

Radicals included by R are more particularly

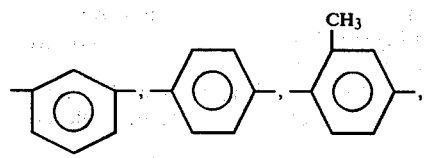

-continued

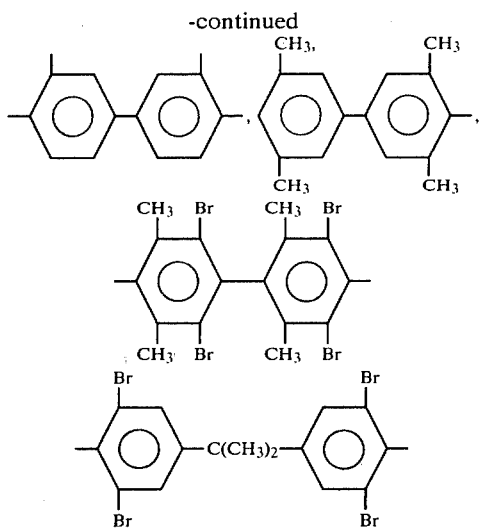

and divalent organic radicals of the general formula,

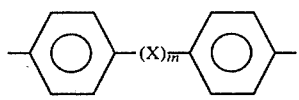

where X is a member selected from the class consisting of divalent radicals of the formulas,

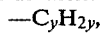

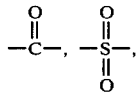

—O—, and —S—, where m is 0 or 1, and y is a whole number from 1 to 5.

Radicals included by $R^1$ are, for example, phenyl, tolyl, xylyl, naphthyl, chlorophenyl, bromonaphthyl, etc., and alkyl radicals, such as methyl, ethyl, etc.

As further shown in U.S. Pat. No. 3,879,428, the aromatic bis(ether phthalimide)s of formula (2) can be made by effecting reaction between phthalimides of the formula,

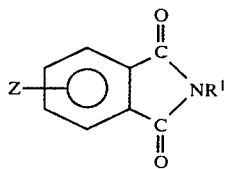 (3)

where Z is a radical selected from the class consisting of nitro, halo, fluoro, bromo, etc., and $R^1$ is as previously defined, and alkali diphenoxide of the formula,

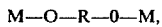 (4)

where R is as previously defined, and M is a metal ion of an alkalide metal selected from the class consisting of sodium, potassium, lithium, etc.

Included by the alkali diphenoxides of formula (4), are sodium and potassium salts of the following dihydric phenols, 2,2-bis(2-hydroxyphenyl)propane;
2,4'-dihydroxydiphenylmethane;
bis-(2-hydroxyphenyl)methane;
2,2-bis-(4-hydroxyphenyl)propane hereinafter identified as "Bisphenol-A" or "BPA",
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfoxide;
4,4'-dihydroxydiphenyl sulfide;
hydroquinone;
resorcinol, etc.

A more complete understanding of the practice of the method of the present invention can be obtained by reference to the drawings when in FIG. 1 there is shown in schematic a method of preparing aromatic bis(ether phthalic anhydride) from an exchange reaction involving an imide-anhydride exchange between molten aromatic bis(ether phthalimide) and aqueous phthalic acid solution, followed by the extraction of the exchange mixture with an organic solvent and the stripping of the aqueous mixture from the extraction column in a thin film evaporator to recover the aromatic bis(ether phthalic anhydride).

Figure 2:
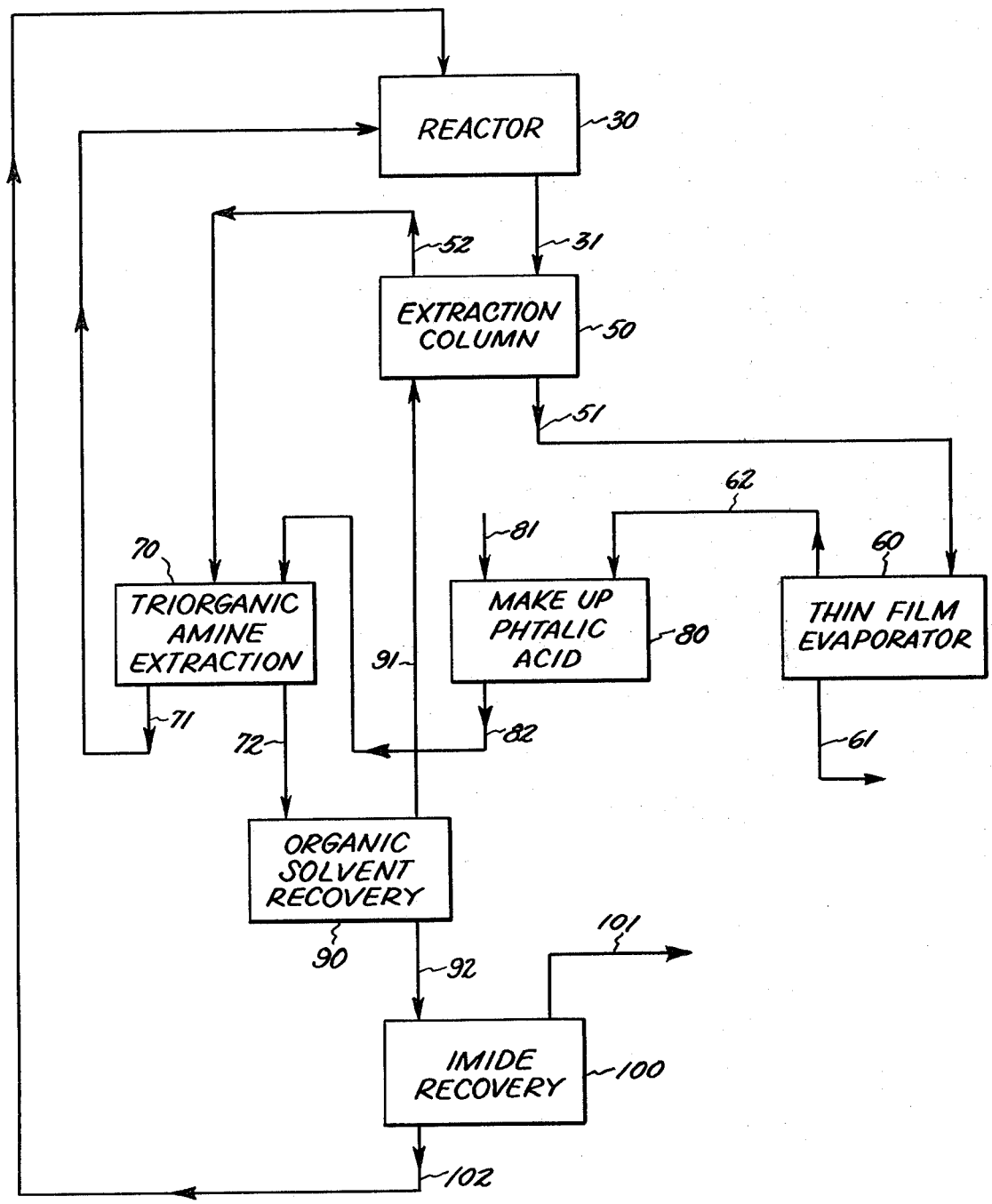

In FIG. 2 there is shown in schematic the recycling of aqueous phthalic acid make-up mixture to extract the triorganoamine from the organic solvent solution recovered at the top of the extraction column. The resulting aqueous phthalic acid solution having the extracted triorganoamine exchange catalyst is then recycled to the reactor while the resulting extracted organic solvent solution is then distilled to recover the organic solvent, unreacted aromatic bis(ether phthalimide) and phthalimide for recycling.

There is shown more particularly in FIG. 1, a bisimide melt tank 10 with an agitator at 11 and a heated feed line 12 which conveys the molten bisimide to reactor 30. Simultaneously an aqueous mixture of phthalic acid and imide-anhydride exchange catalyst is fed into tank 20 via 21 and then passed through heat exchanger 22 before it is conveyed through a heated line to reactor 30. Thorough mixing of the molten bisimide and the aqueous phthalic acid feed, which are maintained at flow rates sufficient to maintain a ratio of 6 moles of phthalic anhydride per mole of bisimide, is achieved by passing the feed stream through a mixing zone 31 prior to entering the reactor 30. The heat exchanger 22 is operated to advance the temperature of the phthalic acid mixture to 200° C. After a residence time in reactor 30 of about 10 minutes or less, the mixture is then fed through a heated line at 33 into holding tank 40. A valve at 32 provides a means for sampling the mixture from reactor 30. The imide-anhydride exchange mixture is then fed through a heated line at 41 to an extraction column 50 at a temperature in the range of about 130°–200° C. Extraction solvent is fed into the bottom of the extraction column after passing through a heat exchanger 42 to bring the solvent up to a temperature of 130° C. to 200° C. prior to being fed into extraction column 50. Suitable extraction solvents are, for example, toluene, benzene, chlorobenzene, o-dichlorobenzene, etc. An organic solvent solution of the imide-anhydride extraction containing, for example, N-organophthalimide, bisimide, etc., is passed through heat exchanger 52 and recovered for recycling. An aqueous exchange mixture is separated at the bottom of extraction column 50 and fed into a vertical thin film evaporator 60 through line 51. Rotating wiper blades at 61 facilitate the evaporation of an aqueous mixture of phthalic acid and imide-anhydride exchange catalysts which is condensed in a heat exchanger 62. The desired bisanhydride in a molten state is recovered at 63.

More particularly there is shown in FIG. 2, an imide-anhydride exchange reactor 30 from which the exchange reaction mixture is fed at 31 into the extraction column at 50. The resulting aqueous imide-anhydride exchange mixture is then fed from the extraction column at 51 into a thin film evaporator 60. At 52, there is recovered the organic solvent phase containing extracted aromatic imides and some of the triorganoamine exchange catalyst which is fed into a triorganoamine extractor 70.

Molten aromatic bis(ether phthalic anhydride) is recovered from the thin film evaporator at 61 while aqueous phthalic acid solution containing triorganoamine exchange catalyst is fed at 62 into a make-up phthalic acid tank 80. Additional phthalic anhydride is introduced at 81 into tank 80 to produce an aqueous phthalic acid mixture having an excess of phthalic acid over triorganoamine catalyst. The aqueous acidic mixture is fed from the line 82 into a triorganic amine extractor 70 resulting in a feed mixture of phthalic acid-triorganic amine which is fed via 71 into reactor 30. The extracted organic solvent is then fed through line 72 into an organic solvent recovery thin film evaporator 90 which feeds the extracted organic solvent back to extraction column 50 through line 91 while the residue is fed via line 92 into an imide recovery stage 100 which effects the separation by thin film evaporation of the phthalimide at 101. The residual aromatic bis(ether phthalimide) in molten state is recovered at 102 and is returned to reactor 30.

In order that those skilled in the art will be better able to practice the present invention, the following example is given by way of illustration and not by way of limitation. All parts are by weight.

EXAMPLE

In accordance FIG. 1 in the drawing, molten 2,2-bis[4-(N-methylphthalimide-4-oxy)phenyl]propane was fed into the reactor filled with Koch static mixers of the Koch Engineering Company, New York, New York, and maintained at a temperature of about 200° C. and 500 psi. Simultaneously, an aqueous solution of phthalic acid and triethylamine having 2 moles of triethylamine per mole of phthalic acid was pumped through a heat exchanger and brought up to a temperature of about 200° C. and fed through a separate line into the reactor. The aqueous phthalic acid mixture was pumped into the reactor at a flow rate sufficient to maintain a ratio of about 4-10 moles of phthalic acid per mole of the aromatic bis(ether phthalimide).

The resulting equilibrated reaction mixture was collected in a holding tank maintained at a temperature of about 70° C.–200° C. and a pressure of about 70 to 300 psi. The equilibrated reaction mixture was then fed into a toluene extraction column maintained at 130°–200° C. and 150–500 psi. After extraction, there was obtained an aromatic bis(ether anhydride) product having at least 97 mole percent of 2,2-bis[4-(3,4-dicarboxyphenoxy)phenyl]propane dianhydride. Recovery of the aromatic bis(ether anhydride) was achieved by feeding the mixture into a thin film evaporator to effect the separation of molten aromatic bis(ether anhydride) at the bottom and aqueous phthalic anhydride mixture at the top.

The above imide-anhydride exchange reaction was repeated several times and the organic solvent fed into the extraction column was analyzed after each extraction of the imide-anhydride exchange mixture to determine whether there was a build-up of the triethylamine in the toluene and if a build-up occurred, whether it had any adverse effect on the ability of the toluene to extract the organic residue from the aromatic bis(ether phthalic anhydride). The following results were obtained which shows the increase of triethylamine concentration in toluene after each run, where $Et_3N$ is triethylamine:

TABLE

| BEFORE EXTRACTION % $Et_3N$ in toluene | AFTER EXTRACTION % $Et_3N$ in toluene |
|---|---|
| 15.18 | 20.70 |
| 17.65 | 24.20 |
| 22.68 | 27.31 |
| 27.03 | 31.52 |
| 87.89 | 89.27 |
| 99.96 | 99.96 |

The above results show that there was a continuous increase in the triethylamine concentration in the toluene which led to a significant loss of catalyst.

An additional study was made in accordance with FIG. 2, utilizing aqueous phthalic acid solutions having about 28% by weight of phthalic acid. The toluene phase having about 10% by weight of triethylamine obtained from the extraction column was extracted with a 35% by weight phthalic acid solution having up to about 25% by weight of triethylamine. It was found that about 85-95% by weight of the triethylamine was removed from the toluene phase. The extracted toluene was further processed by feeding it to a thin film evaporator. Toluene was obtained substantially free of triethylamine which was recycled to the extraction column, while the bottom of the thin film evaporator was further processed to provide aromatic bis(ether phthalimide) and phthalimide.

Although the above example is directed to only a few of the very many variables of the present invention, it should be understood that the present invention is directed to the use of a much broader variety of organic solvents and imide-anhydride triorganoamine exchange catalysts as well as aromatic bis(ether phthalimide) and aromatic bis(ether phthalic anhydride) which are shown in the description preceding this example.

What we claim as new and desire to secure by Letters Patent of the United States is:

1. In the process of making aromatic bis(ether phthalic anhydride) comprising
   (1) effecting an exchange reaction between aromatic bis(ether N-organophthalimide) and phthalic anhydride in the presence of water and triorganoamine exchange catalyst,
   (2) extracting the resulting aqueous exchange reaction mixture with an organic solvent,
   (3) separating the resulting aromatic bis(ether phthalic acid), phthalic acid and triorganoamine catalyst in the aqueous phase from the resulting N-organo phthalimide, unreacted aromatic bis(e- ther N-organophthalimide) and triorganoamine in the organic phase, (4) recovering the aromatic bis(ether phthalic acid) from the aqueous phase and the aromatic bis(ether phthalimide) and N-organo phthalimide from the organic phase, and (5) recycling the phthalic acid and triorganoamine catalyst to the exchange mixture of step (1) and recycling the organic solvent to the extractor of step (2), whereby a constant concentration build-up occurs of the triorganoamine exchange catalyst in the extracting organic solvent, which results in a reduction in the rate of production of the aromatic bis(ether phthalic anhydride), the improvement which comprises, extracting the organic solvent before it is recycled to the extractor of step (2) with an aqueous mixture of phthalic acid and triorganoamine and thereafter recycling the organic solvent to the extractor of step (2), and the aqueous phthalic acid-triorganoamine catalyst to the exchange reaction of step (1) whereby a build-up of the concentration of the triorganoamine in the organic solvent is avoided and a recycling of the recovered triorganoamine exchange catalyst to the exchange reaction is effected.

2. A method in accordance with claim 1, where the triorganoamine exxchange catalyst triethylamine.

3. A method in accordance with claim 1, where the organic solvent is toluene.

4. A method in accordance with claim 1, where the aromatic bis(ether phthalic anhydride) is 2,2-bis[4-(3,4-dicarboxyphenoxy)phenyl]propane dianhydride.

5. A method in accordance with claim 1, where the aromatic bis(ether imide is 2,2-bis[4-(3,4-dicarboxyphenoxy)phenyl]propane-bis-N-methylimide.

6. A method in accordance with claim 1, where the extraction of the organic solvent is effected with an aqueous phthalic acid solution having at least about 20% of phthalic acid.

* * * * *